United States Patent
Blomberg et al.

(10) Patent No.: US 8,713,783 B2
(45) Date of Patent: May 6, 2014

(54) SYSTEM AND METHOD FOR MANUFACTURING BED SUPPORTS FOR CHROMATOGRAPHY COLUMNS

(75) Inventors: Johan Blomberg, Uppsala (SE); Jacek Bielawski, Saltsjobaden (SE)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 0 days.

(21) Appl. No.: 13/060,004

(22) PCT Filed: Aug. 26, 2009

(86) PCT No.: PCT/SE2009/050959
§ 371 (c)(1),
(2), (4) Date: Feb. 21, 2011

(87) PCT Pub. No.: WO2010/024760
PCT Pub. Date: Mar. 4, 2010

(65) Prior Publication Data
US 2011/0146050 A1    Jun. 23, 2011

Related U.S. Application Data

(60) Provisional application No. 61/092,174, filed on Aug. 27, 2008.

(51) Int. Cl.
*B21D 39/06* (2006.01)

(52) U.S. Cl.
USPC ........................................................... 29/509

(58) Field of Classification Search
USPC .......... 29/505, 509, 510, 511; 210/198.2, 656
See application file for complete search history.

(56) References Cited

U.S. PATENT DOCUMENTS

| | | | | |
|---|---|---|---|---|
| 5,419,032 A * | 5/1995 | Rytych | ............................ | 29/511 |
| 5,985,140 A | 11/1999 | Dewaele | | |
| 6,440,301 B1 | 8/2002 | Dobos | | |
| 6,722,012 B1 * | 4/2004 | Texeira et al. | ................... | 29/509 |
| 6,723,447 B1 * | 4/2004 | Braunberger | ............... | 428/542.4 |
| 6,739,169 B2 * | 5/2004 | Baulier | ............................ | 72/312 |
| 6,942,794 B2 * | 9/2005 | Titus et al. | ................. | 210/198.2 |
| 7,043,816 B2 * | 5/2006 | Zaluzec et al. | ................... | 29/460 |
| 7,124,611 B2 * | 10/2006 | Baulier et al. | ................... | 72/220 |
| 7,241,073 B2 * | 7/2007 | Miller et al. | ................... | 403/278 |

(Continued)

FOREIGN PATENT DOCUMENTS

| | | |
|---|---|---|
| CN | 200948371 Y | 9/2007 |
| CN | 201022992 Y | 2/2008 |

(Continued)

OTHER PUBLICATIONS

Search Report from corresponding CN Application No. 200980134134.X dated Dec. 26, 2012.

*Primary Examiner* — David Bryant
*Assistant Examiner* — Justin Sikorski

(57) ABSTRACT

This invention provides a method a method of manufacturing a bed support for a chromatography column is disclosed. The method includes: placing the outer ring of the bed support on a support plate of a machine having a transitional stage; placing the mesh disk into the above ring, pressing another support plate on the mesh disk; rotating the transitional stage; providing a roller attached to the transitional stage with a certain force that is applied over the rim of the ring; and continuously applying the force of the roller onto the ring until a rim of the ring bends then assembles into the mesh disk.

11 Claims, 7 Drawing Sheets

(56) References Cited

U.S. PATENT DOCUMENTS

| | | | |
|---|---|---|---|
| 7,770,778 B2 * | 8/2010 | Hasegawa et al. | 228/173.6 |
| 8,015,688 B2 * | 9/2011 | Chen et al. | 29/509 |
| 2002/0125181 A1 | 9/2002 | Pichl et al. | |
| 2003/0177629 A1 | 9/2003 | Thibault et al. | |
| 2004/0184957 A1 | 9/2004 | Titus et al. | |
| 2006/0075797 A1 | 4/2006 | Baulier et al. | |
| 2009/0134162 A1 * | 5/2009 | Jouillat et al. | 220/270 |
| 2010/0037449 A1 * | 2/2010 | Tresse et al. | 29/505 |
| 2010/0196087 A1 * | 8/2010 | Langer et al. | 403/288 |

FOREIGN PATENT DOCUMENTS

| | | |
|---|---|---|
| CN | 101134161 A | 3/2008 |
| WO | WO 94/23294 | 10/1994 |
| WO | WO 03/005018 | 1/2003 |
| WO | WO 2008/074778 | 6/2008 |

* cited by examiner

SYSTEM AND METHOD FOR MANUFACTURING BED SUPPORTS FOR CHROMATOGRAPHY COLUMNS

CROSS-REFERENCE TO RELATED APPLICATIONS

This application is a filing under 35 U.S.C. §371 and claims priority to international patent application number PCT/SE2009/050959 filed Aug. 26, 2009, published on Mar. 4, 2010 as WO 2010/024760, which claims priority to U.S. provisional patent application No. 61/092,174 filed Aug. 27, 2008.

FIELD OF THE INVENTION

This invention relates to a system and method for implementing a weld free method for manufacturing bed supports for chromatography columns.

BACKGROUND OF THE INVENTION

Generally, chromatography columns are used in industrial processes to purify process liquids and separate substances of interest from process liquids. Currently, chromatography columns comprise a column wall in the form of a hollow column tube, which is connected to a removable upper end plate assembly and a removable lower end plate assembly. One end plate assembly is provided with a process fluid inlet arrangement, typically comprising an inlet pipe and an inlet valve and the other end plate assembly is provided with a process fluid outlet arrangement, typically comprising an outlet pipe and an outlet valve. Each end of the column tube is usually provided in the interior of the column with a removable distribution system. These inlet and outlet distribution systems may be attached to the respective end plate assembly or the upper distribution system may be arranged to be movable towards or away from the end plate assembly.

During use, the space in the column between the distribution systems is usually filled with a chromatography medium. If necessary a retaining mesh may be provided between each distribution system and the media. The inlet distribution system is intended to distribute incoming fluid evenly over the surface of the media at the inlet end of the column while the outlet distribution system is intended to collect fluid evenly from the surface of the media at the outlet end of the column. Such a column may weigh several tons. Typically, the end plate assemblies are bolted to flanges provided at each end of the column. Alternatively, the end plate assemblies may be connected by longitudinal tie bars. Seals are usually provided between the end plates assemblies, inlet and outlet pipes, distribution systems and valves in order to prevent leakage. Columns are typically provided with legs to raise the lower end plate assembly off the ground in order to provide access to the lower end plate assembly, the inlet or outlet pipe and the valve arrangement.

A bed support is typically assembled of an outer ring, a mesh (which could be made of several layers) and for some models of columns an inner ring to which for example a valve could be fitted.

In order to manufacture the bed support of the column, mesh is generally welded to the outer ring in order for the bed support to hold the separation media in the column. The ring is usually made of stainless steel. Even though, the weld produces a good fit between the mesh and bed supports there are problems associated with welding.

The welding process has a tendency to generate a lot of heat, which changes the properties of the stainless steel material and makes it prone to corrosion. This heated stainless steel may begin to corrode, which may allow rust particles and dissolved metal ions to enter into the packing material that sits on top of the bed support. If these impurities originating from corrosion process were to enter the separation media utilized in the column, then the packing material, the separation media, may be considered useless and would need to be replaced. Further, since the welding process causes deterioration of the corrosion resistance of the stainless steel it makes the manufacturing process unreliable, and decreases the yield. The quality of the final product is poor, as the bed support once mounted in the chromatographic column will corrode leaking corrosion products into the substance, which is to be purified.

Therefore, there is a need for a new manufacturing process for assembling a mesh onto a bed support that is reliable, increases the yield and improves the quality of the final product of the bed support.

SUMMARY OF THE INVENTION

The present invention has been accomplished in view of the above-mentioned technical background, and it is an object of the present invention to provide a method for manufacturing a bed support for a chromatography column.

In a preferred embodiment of the invention, a method of manufacturing a bed support for a chromatography column is disclosed. The method includes: placing the outer ring of the bed support on a support plate of a machine having a transitional stage; placing the mesh disk into the above ring, pressing another support plate on the mesh disk; rotating the transitional stage; providing a roller attached to the transitional stage with a certain force that is applied over the rim of the ring; and continuously applying the force of the roller onto the ring until a rim of the ring bends then assembles into the mesh disk. The same procedure is repeated assembling an inner ring would such be required.

In another preferred embodiment of the invention, another method of manufacturing a bed support for a chromatography column is disclosed. The method includes: placing an outer ring of the bed support on a support plate; placing a mesh disk into the ring; pressing another support plate on the mesh disk; rotating the support plate with the outer ring of the bed support; providing a transitional stage carrying the roller; applying certain force that is applied over a rim of the ring; and continuously applying the certain force of the roller until the rim bends then assembles into the mesh disk of the bed support. The same procedure is repeated assembling an inner ring would such be required.

BRIEF DESCRIPTION OF THE DRAWINGS

These and other advantages of the present invention will become more apparent as the following description is read in conjunction with the accompanying drawings, wherein.

DETAILED DESCRIPTION OF THE INVENTION

The presently preferred embodiments of the invention are described with reference to the drawings, where like components are identified with the same numerals. The descriptions of the preferred embodiments are exemplary and are not intended to limit the scope of the invention.

Figure 1:
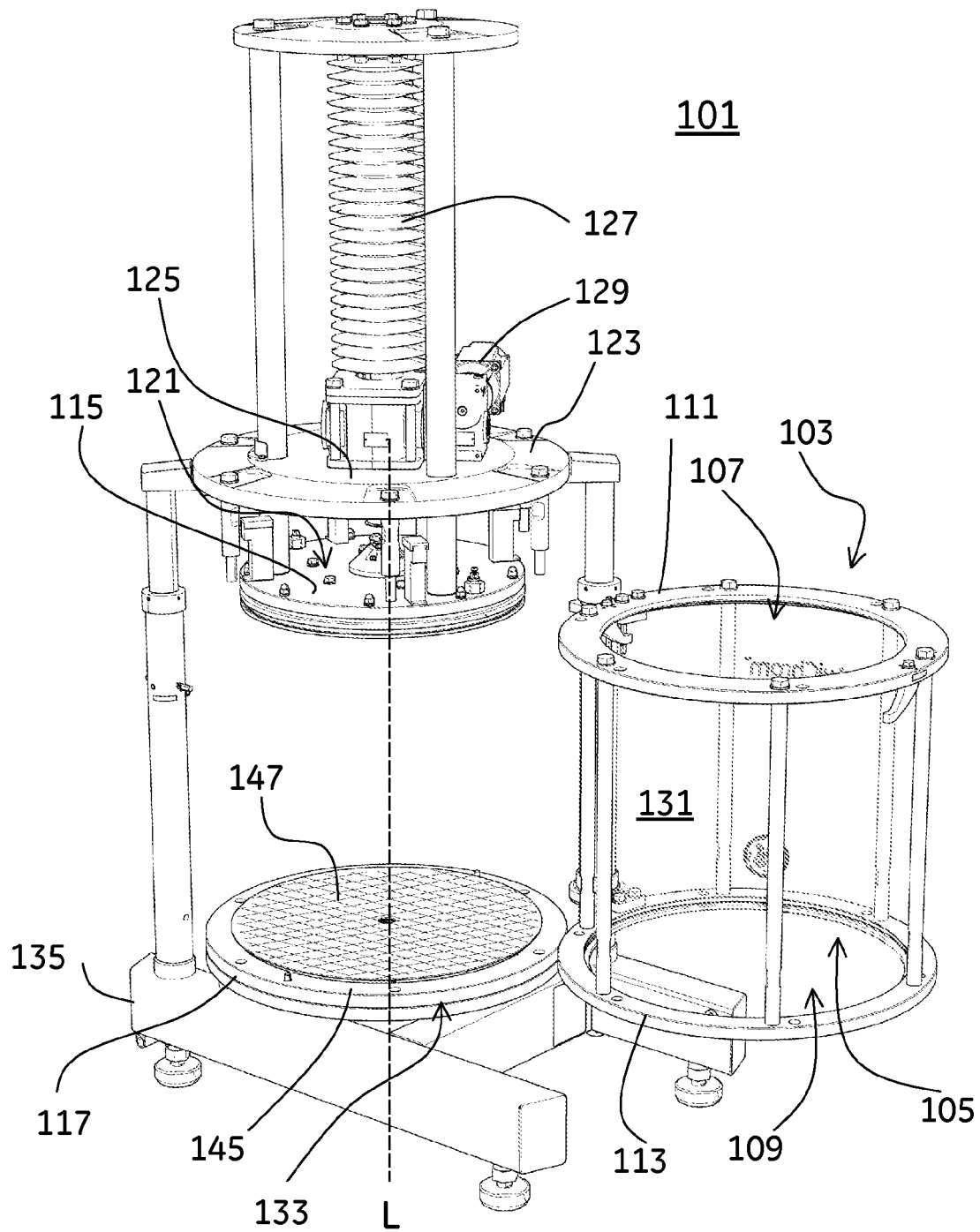
FIG. 1 illustrates a typical Axichrom column in accordance with the invention.

FIG. 1 shows an example of a first embodiment of a chromatography column 101 in accordance with the present invention, which shows a side view of the column after the cylinder wall, has been rotated about axis "L" so that the column wall is no longer positioned between the first and second end plate assemblies. For this invention, the chromatography column 101 includes a bed support 145, which may be manufactured by a method discussed in the flow-chart of FIG. 7. However, this manufacturing method for bed supports is applicable to any chromatography column size, such as columns bigger than the typical Axichrom columns as well as chromatography columns smaller than the Axichrom columns that may have a diameter of 20-30 millimeters or less.

Column 101 comprises a hollow column wall 103, which in this embodiment is in the form of a cylinder 105, with a first open end 107 and a second open end 109. Each open end 107, 109 is provided with an outward projecting circumferential flange 111, respectively 113 arranged perpendicular to the longitudinal axis L of the column wall 103. A first end plate assembly 115 is removably fastened to flange 111 and a second end plate assembly 117 is removably fastened to flange 113. In this embodiment of the present invention the column is intended to be used in the down-flow mode, i.e. the first end plate assembly 115 is intended to be used to feed fluids to the column 101 and the second end plate assembly is intended to be used to remove fluids from the column, however the present invention is equally applicable to columns using the up-flow mode. In use, column wall 103 may be occupied by a chromatography medium (not shown) also known as particles. This chromatography medium sits on a bed support 145 that is attached to a bottom portion of the frame 135. The bed support 145 has a mesh 147 that enables it to hold the chromatography medium. First end plate assembly 115 is provided with the usual fluid feed system 121 (also called "movable adapter") comprising one or more valves, distribution channels, distribution nets, nozzles, connectors, etc which are well-known in the art and which are referenced collectively under the reference number 121. In this example of a column, first end plate assembly 115 comprises first end plate 123, which is removably fastened to flange 111, and which has a central opening 125 through which a hollow shaft 127 is movable in the longitudinal direction of the column by a motor 129. In use, hollow shaft 127 projects into the column cavity 131 and supports the fluid feed system. Motor and drive assembly 129 can be used to move the movable adapter 121 towards and away from first end plate 123 and thereby adjust the depth of movable adapter 121 in the column 101. Second end plate assembly 117 is provided with the usual fluid collecting system 133 comprising one or more valves, distribution channels, distribution nets, nozzles, connectors, etc. which are well-known in the art and which are referenced collectively under the reference number 133. Column 101 is supported in frame 135.

Figure 2:
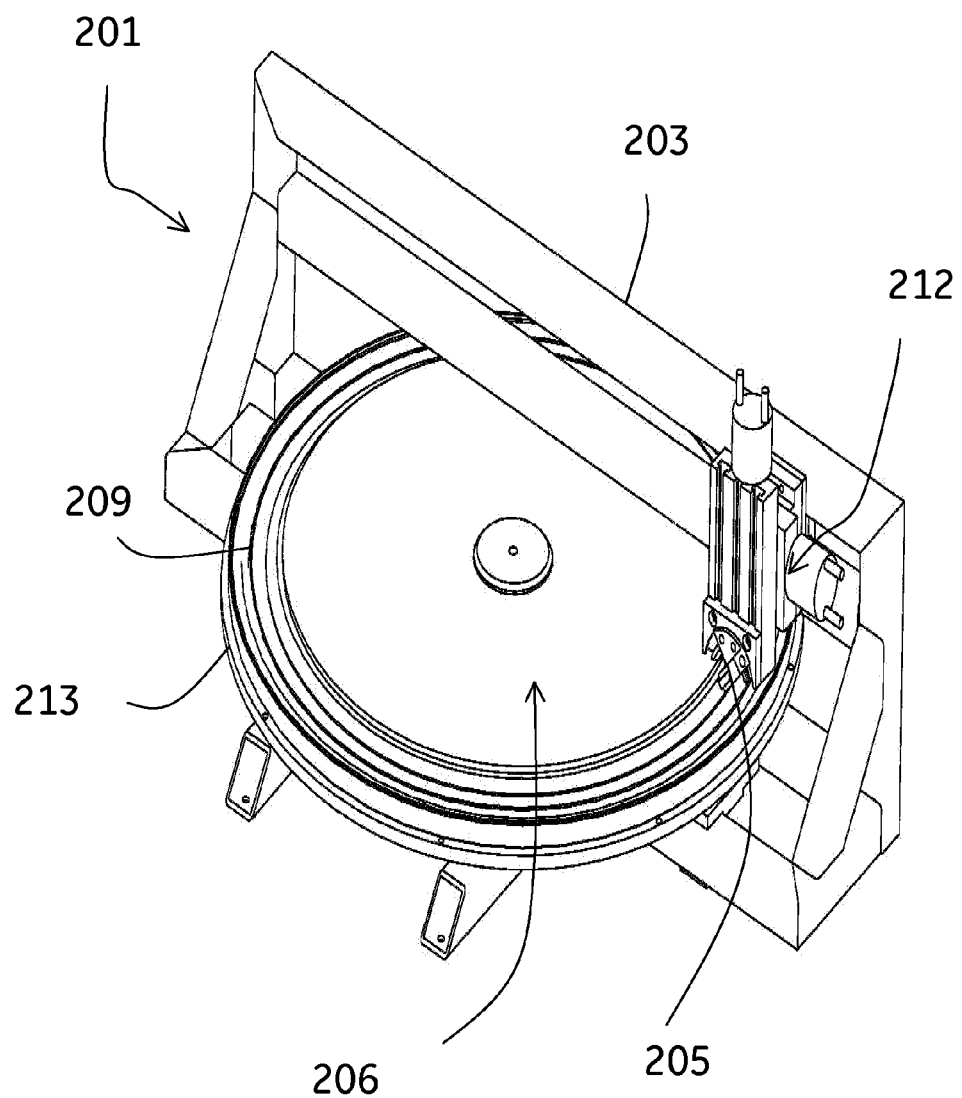
FIG. 2 is a top view of a machine used for a weld free assembly of a bed support in accordance with the invention.

FIG. 2 is a top view of the machine used for the purpose of weld free assembly of a bed support with the bed support 145 of FIG. 1 in accordance with the invention. This machine 201 is similar in terms of function to a typical lathe but here only equipped with the elements needed to perform only here described function. Transitional x, y stage 212 is stationary to the arm 203 and provides means for fine adjustment of a roller 205. Arm 203 is a horizontal arm, which provides means for course adjustment of the position of transitional stage 212. Roller 205 may be a circular wheel or it may be a block of steel, which may be lubricated, or any kind of structure that can be utilized to bend the rim 209. A supporting plate 213 located on the bottom of the bed support 145 is utilized to hold the bed support 145 (FIG. 1) to the rotating device of the machine 201. Another supporting plate 206 is on top of the bed support 145, which is utilized to hold the bed support 145 in place. The ring 204 may be made of any kind of material, such as plastic, stainless steel or any other material known to those of ordinary skill in the art. A bottom portion of the machine 201 include a typical rotating motor connected to typical driver electronics that is utilized to rotate the bed support 145 and/or mesh 147 in a rotating motion. Mesh disk 147 may be made of any kind of polymer; ceramics or it may be made of stainless steel or other metal alloys.

Figure 3:
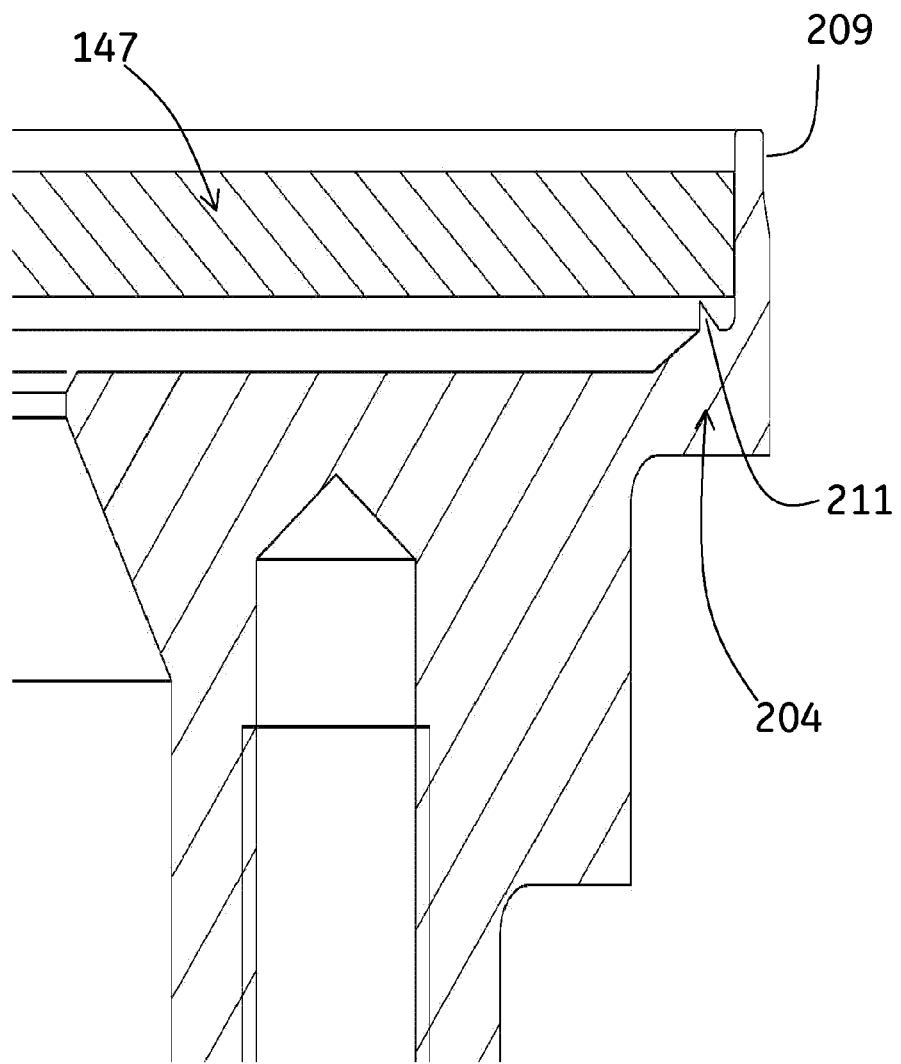
FIG. 3 shows another close-up side view of the ring and the mesh of FIG. 1 in accordance with the invention.
Figure 4:
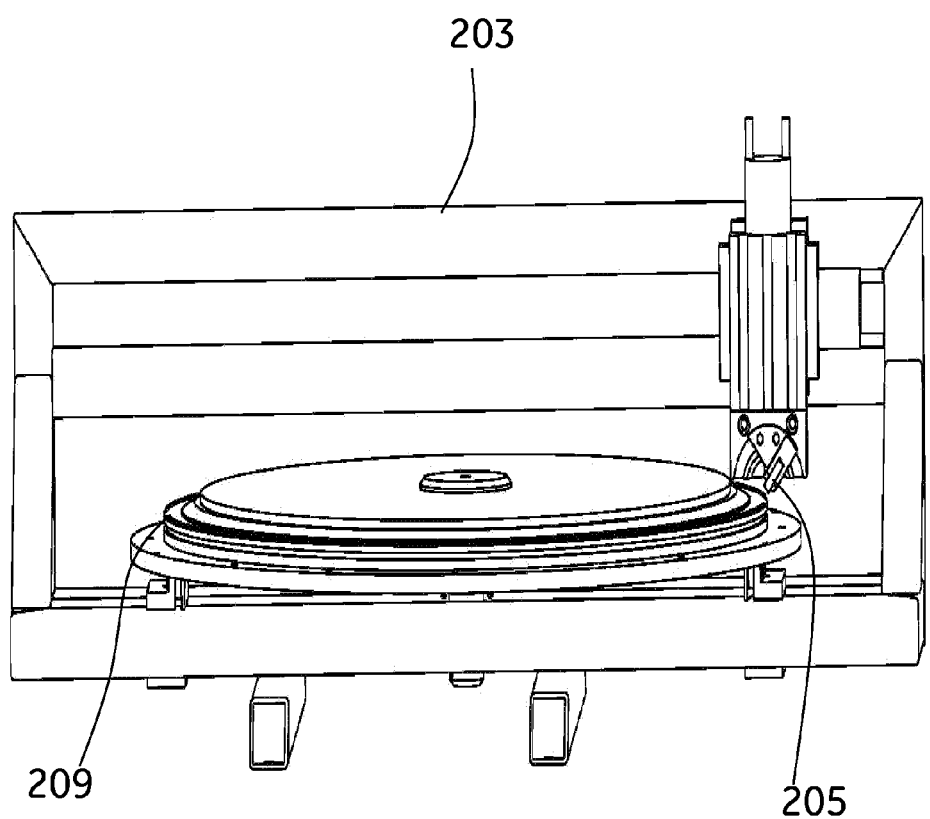
FIG. 4 is a side view of the machine with the with the bed support of FIG. 1 in accordance with the invention.

FIG. 3 shows a portion of the rim 209 and the mesh disk 147 on the outer ring 204. Ring 204 includes a sharp feature 211 that will be utilized to trap an outer portion of the mesh 147 in the ring 204. FIG. 4 is a side view of the machine 201 with the bed support of FIG. 1 in accordance with the invention. In this figure, the roller 205 is close to touching the rim 209 in order to assemble the ring 204 with the mesh disk 147 or mesh 147.

Figure 5:
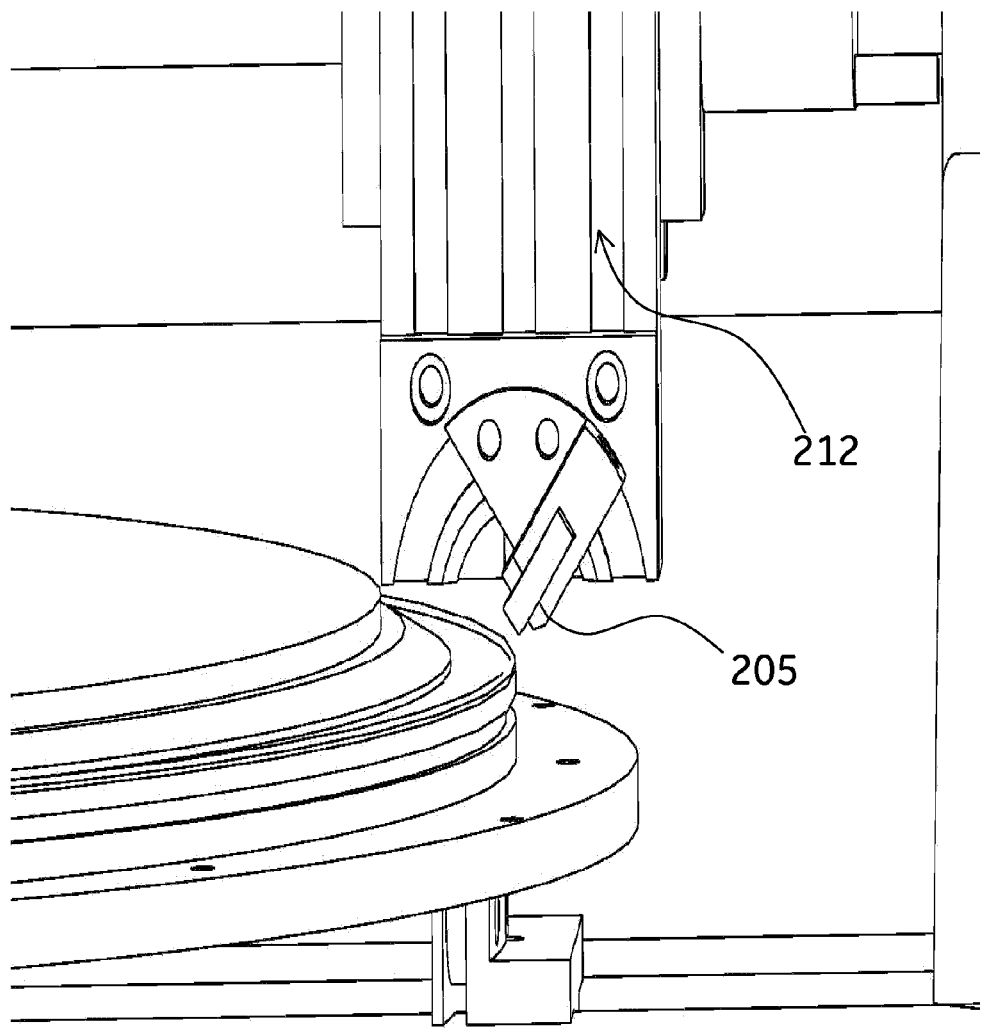
FIG. 5 is a close-up side view of the roller and the bed support of FIG. 1 in accordance with the invention.

FIG. 5 is a close-up side view of the roller and the bed support of FIG. 1 in accordance with the invention. At this point, the transitional stage 212 is utilizing the roller 205 to assert force onto the rim 209 in order for the ring 204 to assemble with the mesh 147. The amount of force being applied by the transitional stage 212 and the roller 205 onto the rim 209 is dependent up on the thickness of the material and the property of the material in question and is such so the rim will be plastically deformed.

In other embodiments of the invention, an outer portion of the ring 204 may be assembled or mounted onto the mesh 147 by first heating the outer portion of the ring 204 then applying a typical force to bend the outer portion of the ring 209 onto the mesh 147. In yet another embodiment of the invention, the outer portion of the ring 204 has sloping edges where force, such as the roller 205 or another applicable force can be applied to this sloping edge to force it to be bent over the mesh 147. In another embodiment of the invention, the outer portion of the ring 204 may be hammered down, then the ring 204 can be put on typical machine that will apply force to the outer portion of the ring 204. The hammer force or any of the forces describe may be applied once on the outer portion of the ring 204 or it may be applied numerous times, such as 5-100 times or more depending on what the user decides. Any method known to those of ordinary skill in the art to bond the outer portion of the ring 204 to the mesh 147 may be utilized in this invention.

Figure 6:
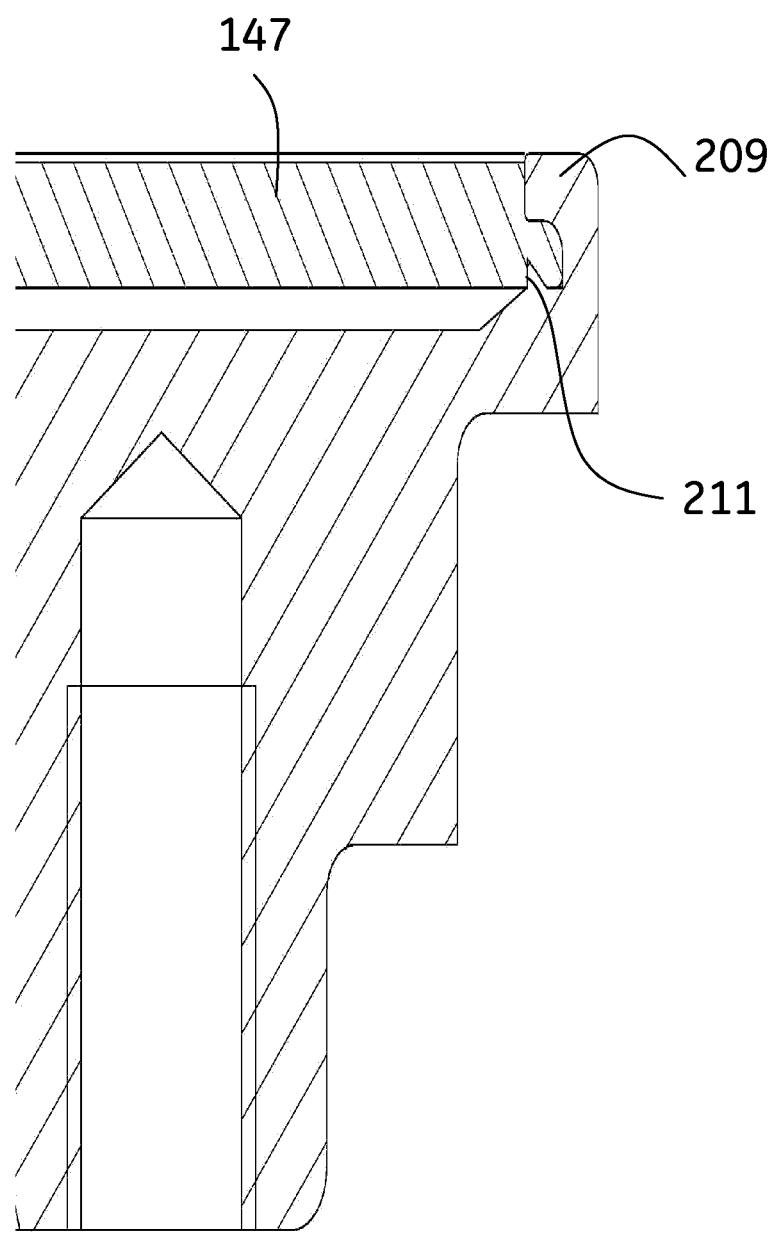
FIG. 6 shows a close-up view of the ring bending over mesh of FIG. 3 in accordance with the invention.

FIG. 6 is another close-up view of the ring 204 and the mesh 147. In this drawing, a rim 209 of the ring 204 has been forced to close on the mesh 147 by plastic deformation of the rim a bending force has been applied by the transitional stage 212 and the roller 205 and the mesh 147 gets trapped and secured in the sharp feature 211 of the ring 204. The rim 209 of the ring 204 is plastically deformed through an action of the roller 205, which causes the rim to bend over the mesh under simultaneous rotation of the ring 204 and the mesh 147. The outer portion of the ring 204 is carefully designed and provided with elements which have a catching and retaining action on the mesh 147 thus preventing it from disengaging and securing the forces needed to firmly grip the mesh 147 inside the ring 204.

Figure 7:
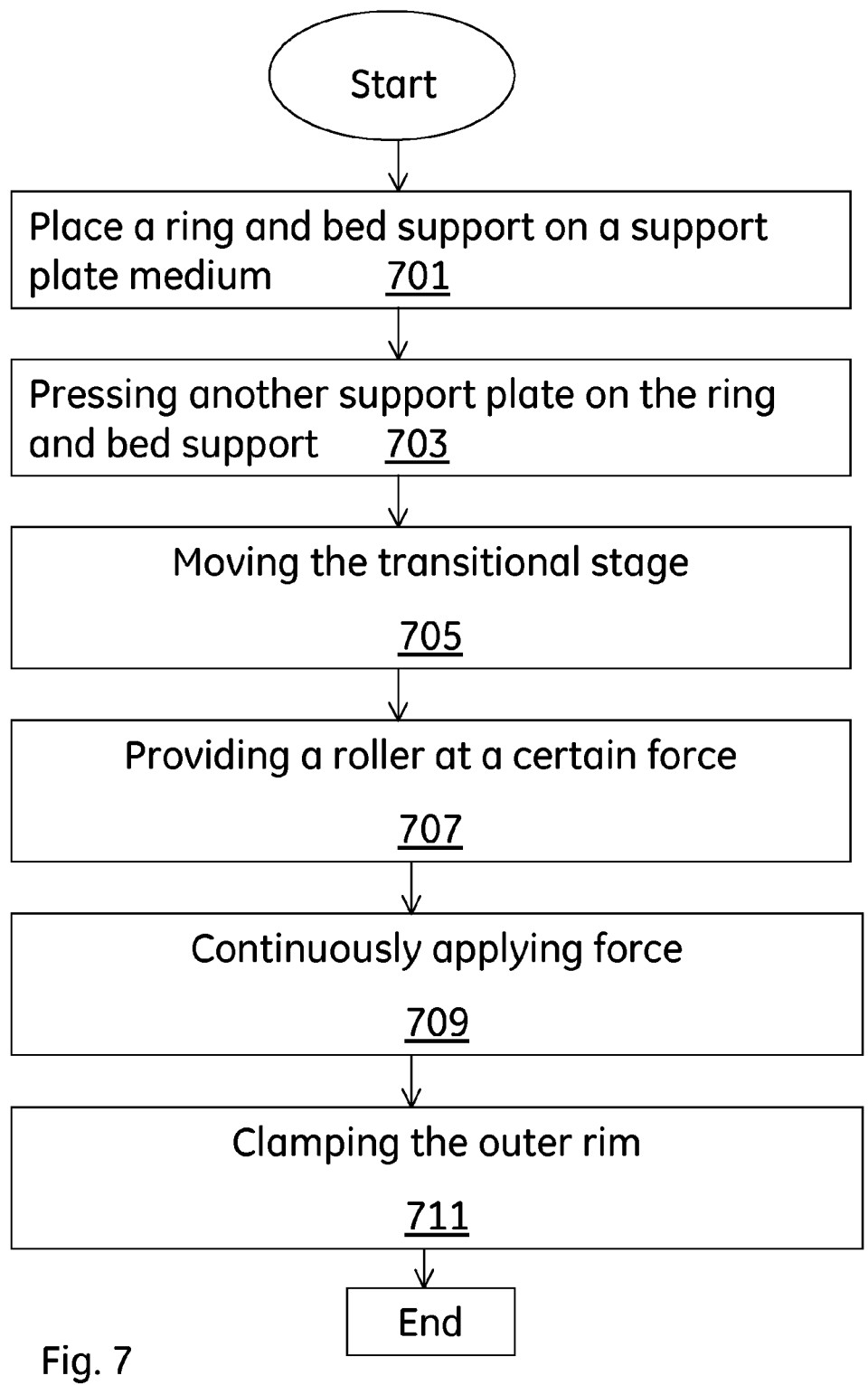
FIG. 7 is a flow-chart that illustrates how the weld free method is manufactured for the bed support of FIG. 1.

FIG. 7 is a flow-chart that illustrates how the weld free method is manufactured for the bed support of FIG. 1. At block 701, a ring 204 (FIG. 2) made of metal and a mesh disk 147 is placed on supporting plate 213 in the machine 201 to be assembled into a bed support 145. Next, at block 703 another support plate 206 is placed on top of the mesh disk 147 and thus securing the bed support 145 in place.

At block 705, a motor (not shown) connected to the bottom portion 207 of the machine 201 moves the transitional stage supporting plate 213 and/or the bed support 145 in a rotational manner. The bed support 145 is rotating at a speed of 5 to 30 m/min. The preferred speed for the rotation of the supporting plate 213 and the bed support is 10 m/min but is strongly dependent up on the choice of material for the ring. In another machine design, the supporting plate 213 could be stationary and the arm 203 and the transitional stage 212 carrying the roller 205 could be made to rotate and perform the same action.

At block 707, the transitional stage 212 becomes active. A roller 205 is attached to the transitional stage 212. The stage 212 moves the roller 205 into contact with the rim 209 and thus exerts pressure on the roller 205, where the roller 205 is forced to touch the ring 209 to force it to assemble, mount or meld with the mesh 147 onto the bed support 145 as shown in FIG. 4. Next, at block 709 the transitional stage 212 continuously exerts force on the roller 205 to press on the rim 209 until the ring 204 assembles with the mesh 147 of the bed support 145 as shown in FIG. 6. As discussed above, various forces may be used instead of the transitional stage 212 and the roller 205 to exert force on the rim 209 of the ring 204 to make it assemble with the mesh 147. The supporting plate 213 and the bed support 145 keeps rotating in a circle until an outer portion of the ring 204 is assembled into the mesh 147 of the bed support 145. Thus, the supporting plate 213 and the bed support 145 can be rotating anywhere between 5-30 m/min 100 times or until the ring 204 assembles with the mesh 147 of the bed support 145.

Next, at block 711 after the rim 209 of the ring 204 is completed the assembly of the bed support 145 is re-clamped in order to get access to a central boss of the bed support 145 and the boss is fastened to the bed support 145 in the same way.

This invention provides a new manufacturing process for assembling a mesh onto a bed support that is reliable, increases the yield and improves the quality of the final product of the bed support. The bed support is placed on a transitional stage where a ring is assembled onto a mesh of a bed support without using any heat. This type of assembly will not create corrosion particles and deterioration of the corrosion resistance of the ring and will not cause damage to the chromatography medium.

Although the present invention has been described above in terms of specific embodiments, many modification and variations of this invention can be made as will be obvious to those skilled in the art, without departing from its spirit and scope as set forth in the following claims.

What is claimed is:

1. A method of manufacturing a bed support for a chromatography column, the bed support including an outer ring having a rim and a sharp feature, the method comprising:
    placing the outer ring of the bed support on a support plate of a machine having a transitional stage with a roller attached thereto,
    placing a mesh disk into the outer ring, and pressing another support plate on the mesh disk,
    rotating the transitional stage such that the roller attached to the transitional stage applies a certain force over the rim of the ring; and
    continuously applying the force of the roller onto the ring until the rim of the ring bends then assembles into the mesh disk whereby the mesh gets trapped and secured in between the bent over rim and the sharp feature.

2. The method of claim 1, wherein the roller is a wheel.

3. The method of claim 1, further comprising increasing the force of the roller as it is applied over the ring.

4. The method of claim 1, wherein the transitional stage is moving in a rotational movement.

5. The method of claim 1, wherein the transitional stage is moving at a certain speed as the transitional stage is rotating the ring.

6. The method of claim 5, wherein the speed is in the range of 5 to 30 m/minute.

7. The method of claim 6, wherein the speed is 10 m/minute.

8. The method of claim 1, wherein the rim of the ring bends into the bed support.

9. The method of claim 1, wherein the ring is made of stainless steel.

10. The method of claim 1, wherein the ring is made of a polymer.

11. A method of manufacturing a bed support for a chromatography column, the method comprising:
    placing an outer ring of the bed support on a first support plate;
    placing a mesh disk into the ring and pressing another support plate on the mesh disk;
    rotating the first support plate with the outer ring of the bed support;
    providing a transitional stage carrying a roller;
    applying a certain force over a rim of the ring; and
    continuously applying the [certain] force of the roller until the rim bends then assembles into the mesh disk of the bed support whereby the mesh gets trapped and secured in between the bent over rim and a sharp feature of the ring.

\* \* \* \* \*